(12) United States Patent
Ratering

(10) Patent No.: US 9,207,639 B2
(45) Date of Patent: Dec. 8, 2015

(54) TRANSFORMING A-SCAN DATA SAMPLES INTO A THREE-DIMENSIONAL SPACE FOR FACILITATING VISUALIZATION OF FLAWS

(71) Applicant: General Electric Company, Schenectady, NY (US)

(72) Inventor: Ralf Ratering, Bruhl (DE)

(73) Assignee: General Electric Company, Schenectady, NY (US)

( * ) Notice: Subject to any disclaimer, the term of this patent is extended or adjusted under 35 U.S.C. 154(b) by 360 days.

(21) Appl. No.: 13/749,023

(22) Filed: Jan. 24, 2013

(65) Prior Publication Data

US 2014/0204702 A1    Jul. 24, 2014

(51) Int. Cl.
| | | |
|---|---|---|
| G01S 15/00 | (2006.01) | |
| G03H 3/00 | (2006.01) | |
| G01N 29/06 | (2006.01) | |
| G01N 29/11 | (2006.01) | |
| G01N 29/22 | (2006.01) | |
| G01S 7/52 | (2006.01) | |
| G06T 7/00 | (2006.01) | |
| G01S 15/89 | (2006.01) | |

(52) U.S. Cl.
CPC ............ G03H 3/00 (2013.01); G01N 29/0609 (2013.01); G01N 29/069 (2013.01); G01N 29/0645 (2013.01); G01N 29/11 (2013.01); G01N 29/226 (2013.01); G01S 7/52071 (2013.01); G01S 7/52073 (2013.01); G01S 15/8993 (2013.01); G06T 7/0004 (2013.01); G01S 15/8925 (2013.01); G06T 2207/10081 (2013.01); G06T 2207/30164 (2013.01)

(58) Field of Classification Search
USPC .......................................................... 367/8
See application file for complete search history.

(56) References Cited

U.S. PATENT DOCUMENTS

| | | | |
|---|---|---|---|
| 5,189,915 A * | 3/1993 | Reinhart et al. ................ 73/623 |
| 5,787,889 A | 8/1998 | Edwards et al. |
| 7,775,982 B2 | 8/2010 | Hazard et al. |
| 8,365,603 B2 * | 2/2013 | Lesage et al. .................. 73/623 |
| 8,657,605 B2 * | 2/2014 | Wallace et al. ............... 434/219 |
| 8,805,625 B2 * | 8/2014 | Zhang et al. .................... 702/39 |
| 2004/0021858 A1 * | 2/2004 | Shima et al. ............... 356/241.1 |
| 2005/0022602 A1 * | 2/2005 | Falsetti et al. .................. 73/627 |
| 2005/0156364 A1 * | 7/2005 | Bisiaux et al. .................. 266/79 |
| 2006/0241434 A1 * | 10/2006 | Shimazaki .................... 600/437 |
| 2006/0291710 A1 * | 12/2006 | Wang et al. ................... 382/131 |
| 2008/0069422 A1 * | 3/2008 | Wang et al. ................... 382/132 |

(Continued)

FOREIGN PATENT DOCUMENTS

WO     2012112898 A1    8/2012

OTHER PUBLICATIONS

PCT Search Report & Written Opinion issued Apr. 16, 2014 in connection with corresponding PCT Patent Application No. PCT/US2014/011589.

*Primary Examiner* — James Hulka

(74) *Attorney, Agent, or Firm* — Barclay Damon, LLP

(57) ABSTRACT

Various approaches are described for visualizing one-dimensional A-scan data samples in a three-dimensional space. Each of the data samples represents ultrasonic signals received from a test material. The data samples are transformed into the three-dimensional space as a geometric shape corresponding to a relative amount of ultrasonic energy reflected back from the test material. The data samples as transformed into the three-dimensional space with the geometric shapes rendered therein can be displayed.

26 Claims, 9 Drawing Sheets

(56) References Cited

U.S. PATENT DOCUMENTS

| | | | |
|---|---|---|---|
| 2008/0146938 A1* | 6/2008 | Hazard et al. | 600/462 |
| 2009/0301202 A1* | 12/2009 | Bisiaux et al. | 73/622 |
| 2010/0064811 A1* | 3/2010 | Kroning et al. | 73/628 |
| 2010/0307249 A1 | 12/2010 | Lesage et al. | |
| 2011/0087443 A1 | 4/2011 | Zhang et al. | |
| 2012/0230566 A1* | 9/2012 | Dean et al. | 382/131 |

* cited by examiner

TRANSFORMING A-SCAN DATA SAMPLES INTO A THREE-DIMENSIONAL SPACE FOR FACILITATING VISUALIZATION OF FLAWS

BACKGROUND OF THE INVENTION

The present invention relates generally to non-destructive testing, and more particularly, to transforming one-dimensional A-scan data samples into a three-dimensional space to facilitate three-dimensional visualization of any flaws present in a test material undergoing non-destructive testing.

Non-destructive testing can entail a multiple of analysis techniques used to evaluate the properties of a material, component or system ("test material") without causing damage thereto. Ultrasonic testing is one type of non-destructive testing modality that uses high frequency sound energy to conduct examinations of a test material. A typical ultrasonic testing inspection system used to locate flaws in a test material such as a weld on piping and tubing can include a handheld ultrasonic probe that contains a pulser/receiver and a transducer. The pulser/receiver produces electrical pulses that drive the transducer to generate ultrasonic energy. The ultrasonic energy is introduced to the test material and propagates therethrough in the form of waves or beams. When there is a discontinuity such as a flaw (e.g., a crack) in the beam path, part of the energy will be reflected back from the flaw to the surface of the test material. The reflected waves of ultrasonic energy are converted into electrical signals ("ultrasonic signals") and can be displayed on a screen of a display device that is associated with the ultrasonic testing inspection system.

An A-scan is one type of display format that can be used to present the ultrasonic signals reflected from the test material. The A-scans are generally one-dimensional in that each scan plots the reflected signal strength representative of the amount of received ultrasonic energy against the time from signal generation to when an echo was received by the transducer. An ultrasonic inspection specialist can examine the A-scans to detect the existence of any flaws in the test material based on the location, size, and orientation of any reflectors appearing in the scans.

It can be a difficult task for an ultrasonic inspection specialist to interpret A-scans and accurately ascertain whether a flaw is present in the test material. Locating flaws in an A-scan is a difficult task, because noise signals and geometry echoes may obfuscate the ultrasonic signals caused by actual defects. This issue is compounded for ultrasonic testing inspection systems that use two-dimensional probe arrays to scan test material. In particular, the ultrasonic data acquired by a two-dimensional probe array is three-dimensional by nature because the orientation of the beam of ultrasonic energy generated therefrom is defined by two dynamic angles instead of one dynamic angle as with a standard phased-array probe. Typical A-scans generated from presently available ultrasonic testing inspection systems are not able to display the three-dimensional information embodied in the ultrasonic signals acquired by a two-dimensional probe array.

Some A-scans generated from ultrasonic testing inspection systems can display a top view, a side view and an end view of the ultrasonic signals. In this case, the top view, the side view and the end view are projected onto a two-dimensional image plane next to each other, such that the views are disparate and separate. The top view, side view and end view all contain maximum intensity projections obtained from fixed angles to present the acquired ultrasonic data. There is no depth information provided with these views. This makes it almost impossible for the ultrasonic inspection specialist to locate the actual position of the data in a three dimensional space in a single image. To determine the position of a reflected signal in the test material, information from multiple images (i.e., the top, side and end views) has to be combined in a mental model and set into relation to the inspected test geometry by the ultrasonic inspection specialist. This is a complicated task that requires intensive training and years of experience and practice. As a result, it is very difficult for the ultrasonic inspection specialist to ascertain if and where a flaw is present in a certain test material and what the flaw looks like. Consequently, the ultrasonic inspection specialist will have to utilize a computational intensive volume reconstruction algorithm that can reconstruct the physical beam geometry (i.e., the beam spread) in a three-dimensional display.

BRIEF DESCRIPTION OF THE INVENTION

In one aspect of the present invention, a method is provided. In this aspect of the present invention, the method comprises: obtaining a plurality of one-dimensional A-scan data samples from an ultrasonic probe, each data sample representing ultrasonic signals received from a test material undergoing non-destructive testing, wherein each data sample indicates an amount of ultrasonic energy received from the test material at a time of occurrence; transforming the plurality of data samples into a three-dimensional space, wherein each of the plurality of data samples are rendered as a geometric shape in the three-dimensional space; and displaying the plurality of geometric shapes.

In a second aspect of the present invention, an ultrasonic testing inspection system is disclosed. In this aspect, there is an ultrasonic probe configured to scan a test material with a beam of ultrasound energy that propagates therethrough and receive ultrasonic signals reflected back from the test material, wherein the ultrasonic signals contain a volume of data representative of the test material. A computing unit is configured to receive the ultrasonic signals from the ultrasonic probe in a form of a plurality of one-dimensional A-scan data samples. Each data sample indicates an amount of ultrasonic energy received from the test material at a time of occurrence. The computing unit is further configured to transform the data samples into a three-dimensional space, wherein each of the data samples are rendered as a geometric shape in the three-dimensional space. The ultrasonic testing inspection system also comprises a display unit configured to generate a display in real-time of the geometric shapes.

In a third aspect of the present invention, there is disclosed a non-transitory computer readable medium storing computer instructions, which when executed, enables ultrasonic testing inspection system to perform a method for visualizing a plurality of one-dimensional A-scan data samples in a three-dimensional space. The method comprises: obtaining a plurality of one-dimensional A-scan data samples from an ultrasonic probe, each data sample representing ultrasonic signals received from a test material undergoing non-destructive testing, wherein each data sample indicates an amount of ultrasonic energy received from the test material at a time of occurrence; transforming the plurality of data samples into a three-dimensional space, wherein each of the plurality of data samples are rendered as a geometric shape in the three-dimensional space without reconstructing a physical beam geometry; and generating a display that visualizes the geometric shapes.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

DETAILED DESCRIPTION OF THE INVENTION

Various embodiments of the present invention are directed to three-dimensional visualization of one-dimensional A-scan data samples (hereafter, "data samples") containing ultrasonic signals. In these embodiments of the present invention, the data samples are transformed into a three-dimensional space and rendered therein as geometrical objects. The size and color of the geometrical objects can represent the amplitude of the ultrasonic signals in the data samples. Furthermore, the geometrical objects representative of the ultrasonic signals in the data samples can appear in the three-dimensional space in a location representative of the actual location within a material that they were generated, e.g., the location where a reflection occurred. The various embodiments of the present invention can provide three-dimensional visualization of the data samples without having to reconstruct volume data based on the physical geometry of the beams of ultrasonic energy used to scan a test material. That is, the various embodiments of the present invention do not model the actual three-dimensional shape of the beams inside the material from the data samples. Instead, each sample is displayed at its three-dimensional position as a separate geometric object representing amplitude.

This simplifies the process of locating flaws in the material. As a result, the various embodiments of the present invention are suitable for use with two-dimensional probe arrays that can generate three-dimensional data with the limitation of current visualization techniques that make it difficult for ultrasonic inspection specialists to locate the actual position of any of the data in a three-dimensional space. In addition to two-dimensional probe arrays, the various embodiments are suitable for use with other ultrasonic probes, such as for example, one-dimensional phased-array probes or single transducer probes.

Figure 1:
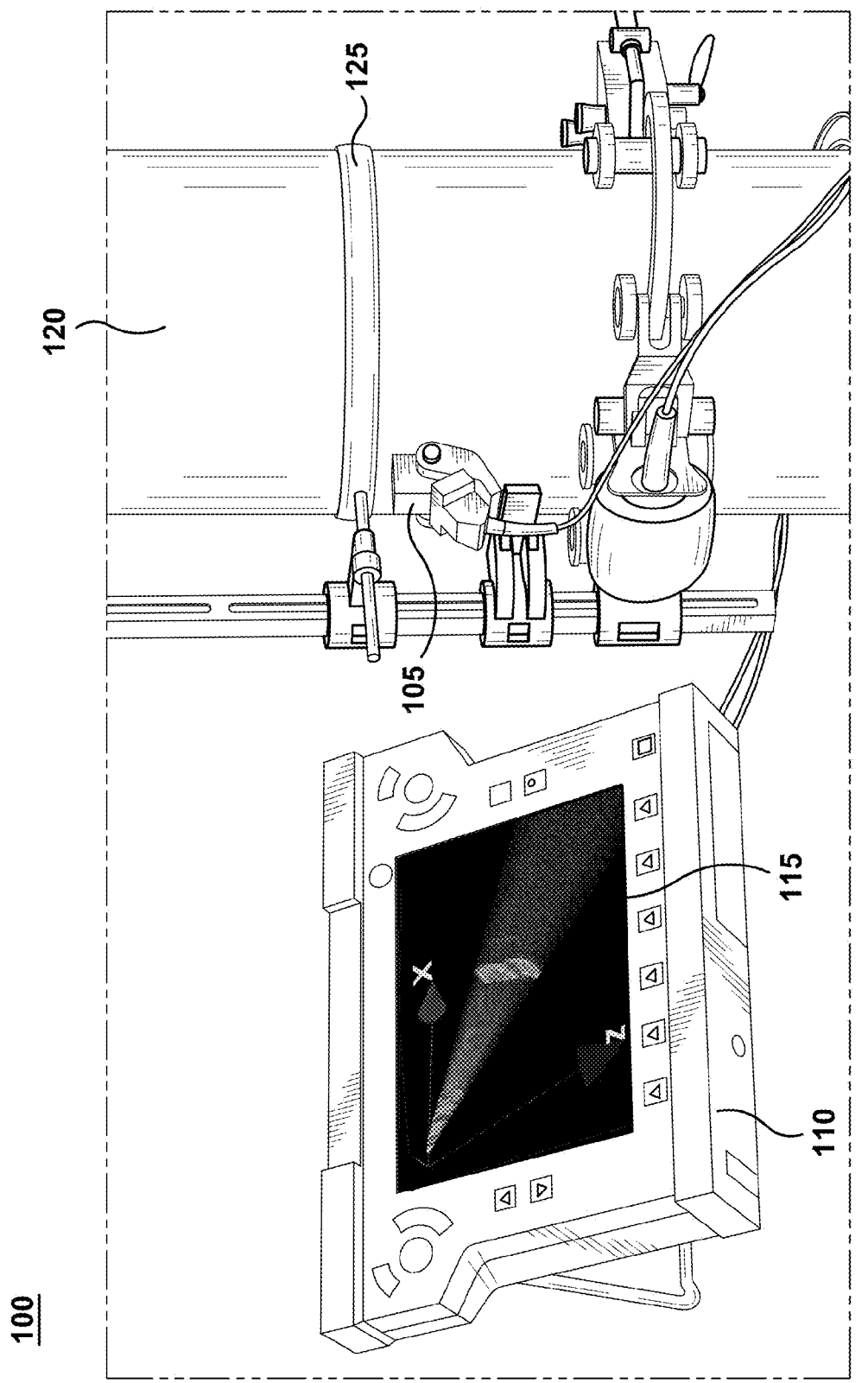
FIG. 1 shows an ultrasonic testing inspection system according to an embodiment of the present invention.

Referring now to the figures, FIG. 1 shows an ultrasonic testing inspection system 100 according to an embodiment of the present invention. The ultrasonic testing inspection system 100 includes an ultrasonic probe 105 and a computing unit 110 with a display unit 115 that operate in conjunction with the probe to perform a non-destructive testing operation on a test material 120. In one embodiment, ultrasonic testing inspection system 100 can be used to examine test material 120 for flaws or defects (e.g., cracks) in the material.

As shown in FIG. 1, test material 120 can be piping or tubing (e.g., steel piping) that is used to transport any one of a number of items. In one embodiment, ultrasonic testing inspection system 100 can be used to inspect a weld 125 in the piping for flaws. Embodiments of the present invention are not limited to inspecting welds in piping. Instead, the various embodiments of the present invention are suitable for use with any material, component or system ("test material") where it is desirable to employ ultrasonic testing inspection techniques to inspect, examine, or evaluate, the properties of the material.

In one embodiment ultrasonic testing inspection system 100 can be a portable device that is used on-site to inspect test material. Embodiments of the present invention are not limited to portable ultrasonic testing inspection systems. Instead, the various embodiments of the present invention are suitable for use with any ultrasonic testing inspection system that utilizes a display unit to view ultrasonic signals generated from an ultrasonic probe in order to ascertain the presence of flaws in material undergoing ultrasonic testing.

Generally, an ultrasonic inspection specialist can use computing unit 110 of ultrasonic testing inspection system 100 to develop and deploy an ultrasonic inspection workflow of test material 120 with ultrasonic probe 105. During an ultrasonic inspection, computing unit 110 can instruct the pulser/receiver of ultrasonic probe 105 to produce electrical pulses that drive the probe's transducer to generate ultrasonic energy that is directed into test material 120. The ultrasonic energy propagates through test material 120 in the form of waves or beams. If there is any flaw or defect in the beam path, part of the energy will be reflected back from the flaw or defect to the surface of test material 120. The reflected wave of ultrasonic energy is converted into electrical signals by the transducer of ultrasonic probe 105. Ultrasonic probe 105 can have a digitizer, e.g., analog to digital converter(s), ADC, that digitizes the ultrasonic signals for transmission to computing unit 110, or computing unit 110 may receive analog signals from ultrasonic probe 105 and computing unit 110 can have a digitizer.

Computing unit 110 is configured to receive the digitized (or analog) electrical signals from ultrasonic probe 105 and perform a multitude of processing operations to facilitate inspection of test material 120 for flaws. In one embodiment, computing unit 110 can receive the digitized ultrasonic signals from ultrasonic probe 105 in the form of one-dimensional A-scan data samples. The data samples can be presented to the ultrasonic inspection specialist through a display generated from display unit 115 that indicates an amount of ultrasonic energy received from the test material at a time of occurrence. As explained below in more detail, computing unit 110 is configured to transform the data samples into a three-dimensional space, such that the data samples are rendered as geometric shapes in the three-dimensional space. The three-dimensional visualization of the data samples generated from display unit 115 enables the ultrasonic inspection specialist to quickly and accurately assess in near real-time during the non-destructive testing operation whether test material 120, including weld 125, contains any flaws.

Those skilled in the art will appreciate that ultrasonic testing inspection system 100 can perform other functions that facilitate the non-destructive testing of test material 120. For example, ultrasonic testing inspection system 100 can include capabilities such as creating inspection plans for inspecting test material 120. These inspection plans can be dependent on the site of the test material, the geometry (e.g., diameter, thickness) of the material and the composition of the material. Other capabilities that ultrasonic testing inspection system 100 can perform include calibrating ultrasonic probe 105 and performing analysis and reporting upon acquiring the ultrasonic signals from the probe. Further capabilities include archiving the ultrasonic signals, analysis and reporting, and sharing these items with other workstations and host computers networked with ultrasonic testing inspection system 100.

Figure 3A:
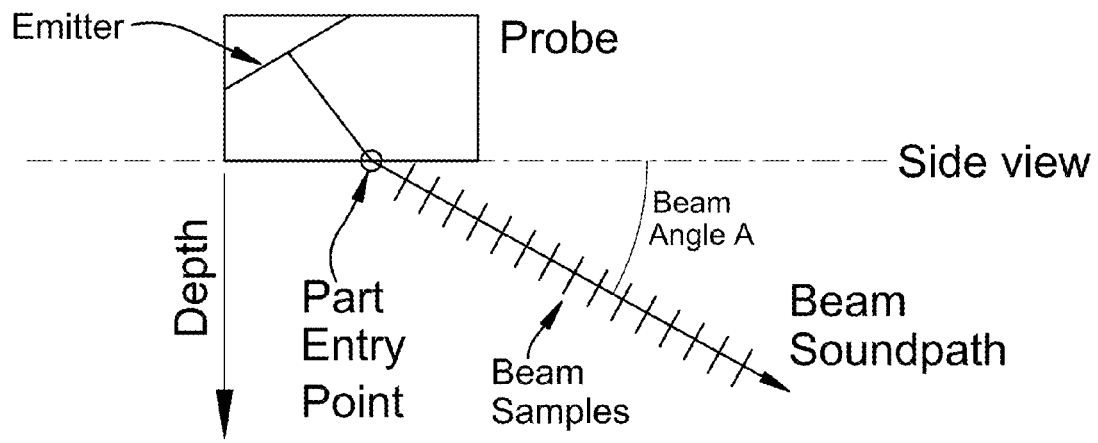
FIGS. 3A-3B illustrate the steering of beams of ultrasonic energy in a test material with a two-dimensional probe array in use with the ultrasonic testing inspection system depicted in FIG. 1.
Figure 3B:
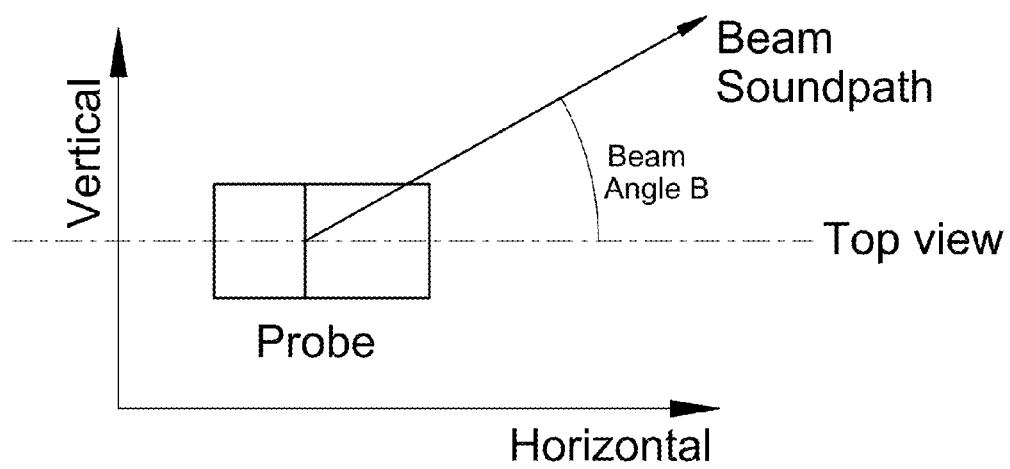

Regarding the aspect of providing three-dimensional visualization of data samples, the various embodiments of the present invention can have applicability with ultrasonic probes that take the form of two-dimensional probe arrays. A typical two-dimensional probe array will steer one or more beams of ultrasonic energy, each in arbitrary direction defined by two angles. In particular, one beam of ultrasonic energy will be steered according to a first beam angle defined between the surface being scanned and the depth that the beam extends into the test material from the surface (as discussed below at least in relation to FIG. 3A) and a second beam angle defined along an orientation line of the probe with the propagation of the beam within the material as viewed from a top view (as illustrated in FIG. 3B). As a result, ultrasonic signals acquired by the two-dimensional probe array will contain a volume of data representative of the test material.

Conventional ultrasonic testing inspection systems are not presently able to display the three-dimensional information embodied in the ultrasonic signals acquired by a two-dimensional ultrasonic probe array. The displays of some ultrasonic testing inspection systems can generate a top view, a side view and an end view of the ultrasonic signals, with each view being projected onto a two-dimensional image plane such that the views are disparate and separate from each other. In this manner, the top view, the side view and the end view all contain maximum intensity projections obtained from a fixed angle. There is no depth information provided with this view. This makes it almost impossible for the ultrasonic inspection specialist to locate the position of the ultrasonic data in a three-dimensional space in a single image. To determine the origin of a reflected signal in the material, the information from multiple images (i.e., the top, side and end views) has to be combined in a mental model and set into relation to the inspected test geometry by the ultrasonic inspection specialist. This is a complicated task that requires intensive training and years of experience and practice. As a result, it is very difficult to ascertain if and where a flaw is present in the test material and what the flaw looks like. Consequently, the ultrasonic inspection specialist would have to utilize a computationally intensive volume reconstruction algorithm that can reconstruct the physical beam geometry (i.e., the beam spread) in a three-dimensional display.

The various embodiments of the present invention can provide a three-dimensional visualization of the ultrasonic signals generated from a two-dimensional ultrasonic probe array without having to utilize a computational intensive volume reconstruction algorithm that reconstructs the physical beam geometry. Although the present invention has particular utility with two-dimensional ultrasonic probe arrays, embodiments described herein are suitable for use with one-dimensional phased arrays, and any other ultrasonic probes that are capable of acquiring ultrasonic signals that capture a volume of data representative of the test material from a three-dimensional perspective.

Figure 2:
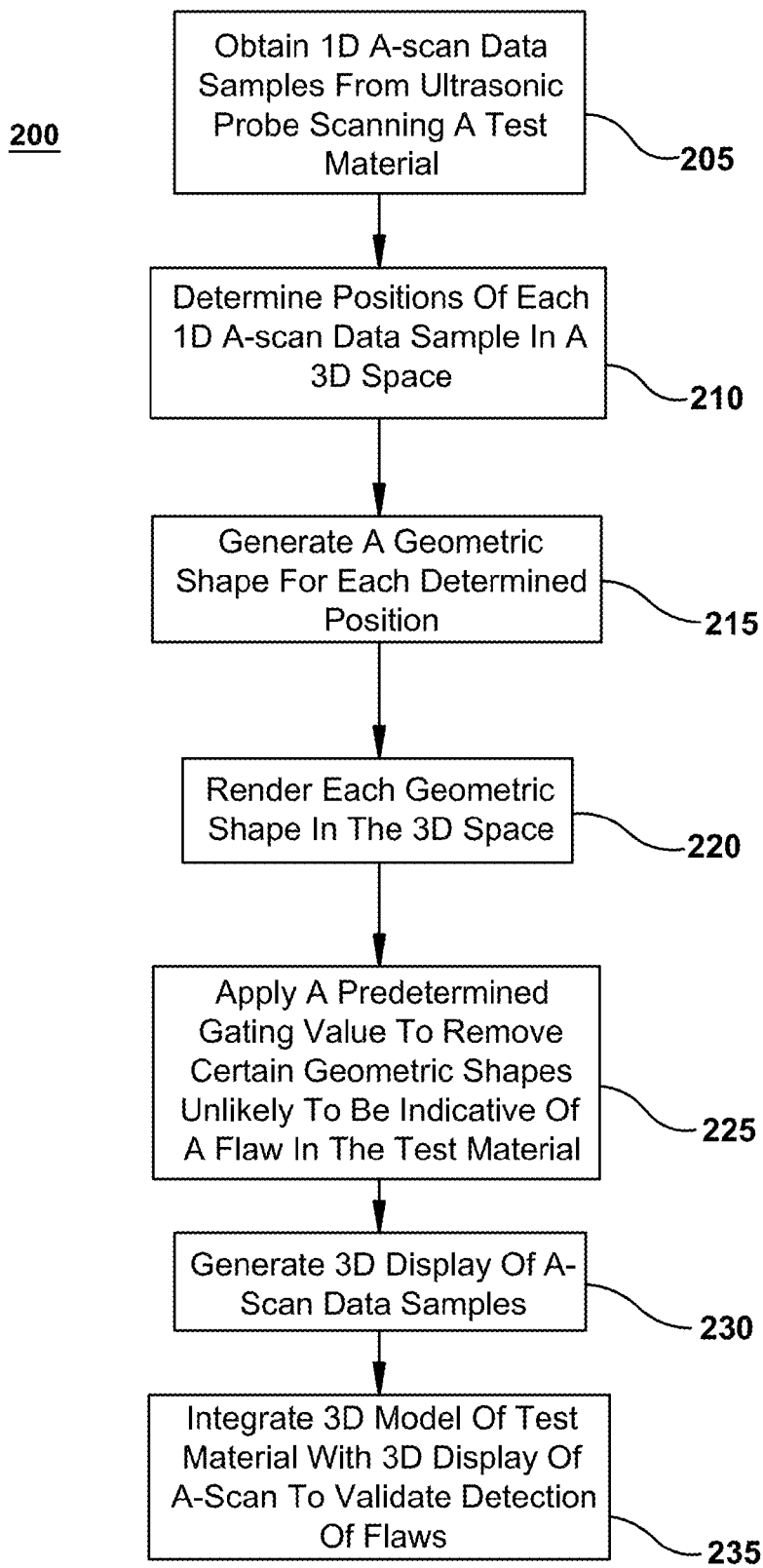
FIG. 2 shows a flow chart describing a method that uses the ultrasonic testing inspection system depicted in FIG. 1 to visualize a plurality of one-dimensional A-scan data samples in a three-dimensional space according to an embodiment of the present invention.

FIG. 2 shows a flow chart 200 describing a method that can use ultrasonic testing inspection system 100 to visualize one-dimensional A-scan data samples in a three-dimensional space. Flow chart 200 begins by obtaining one-dimensional A-scan data samples from an ultrasonic probe that is scanning a test material at 205. In one embodiment, the data samples can include ultrasonic signals that are obtained from the ultrasonic probe during a non-destructive testing operation of the test material. Each data sample can indicate an amount of ultrasonic energy received from the test material at a time of occurrence.

In flow chart 200, the data samples can be transformed into a three-dimensional visualization at 210 by first determining a position that each sample will have in a three-dimensional space. The position of each sample can be representative of a location of a point of reflection within the test material. In one embodiment, the position that each sample will have in a three-dimensional space is computed as a function of: (i) a beam entry point, where the beam of ultrasonic energy (generated from the ultrasonic probe) entered the test material, (ii) beam angles that indicate direction of travel of the beam of ultrasonic energy in the test material (upon transmission through a surface of the test material), and (iii) velocity of sound of the beam of ultrasonic energy in the test material. More specifically, one or a combination of ultrasonic probe 105 or computing unit 110 will measure the time between sending and receiving the signal (time of flight) and the intensity of the reflection. The direction of the sound path in the test material depends on the shape of the wedge that is used to send the signals into the material and is specified by two angles A and B. FIGS. 3A-3B illustrate the direction of the sound path for angles A and B for a two-dimensional probe array that can be used to scan the test material. As shown in FIG. 3A, beam angle A is defined between the surface being scanned and the depth that the beam extends into the test material from the surface. In FIG. 3B, beam angle B is defined along an orientation line of the probe with the propagation of the beam within the material as viewed from a top view looking down at the scanned surface. Referring back to block 210 of FIG. 2, the position of data samples along the beam path in the material is computed by formulating a simple geometrical equation that takes into account the entry point, the time of flight, and the angles A and B.

For each determined position, a geometric shape is generated at 215. Generating geometric shapes in this manner can be achieved by using commercially available graphic packages. Embodiments of the present invention are not limited to any particular type of geometric shape. Those skilled in the art will appreciate that the geometric shape selected to represent a position in the three-dimensional space can be any shape characterized by rectilinear or curvilinear lines or figures used in geometry (e.g., a polygon). The geometric shape corresponding to each determined position can be characterized by a certain size and color corresponding to an amplitude value indicative of the relative amount of received ultrasonic energy, e.g., the intensity of the reflection, associated with that determined position. In one embodiment, larger-sized geometric shapes are indicative of larger amplitude values as compared to smaller-sized geometric shapes that are indicative of smaller amplitude values. Those skilled in the art will appreciate that this is only one example of how size and color of the geometric shapes can be used to represent the amplitude values of ultrasonic signals embodied in the one-dimensional A-scan data samples. Other possible designations of sizes and colors of the geometric shapes are within the scope of the present invention.

Regardless of what designation is used, a color map can be used in one embodiment to map an amplitude to particular sized-geometric shape with a color. The geometric shape size and color can correspond to the amount of ultrasonic energy reflected in the amplitude value. In this embodiment, the color map could contain a plurality of colors, each corresponding to particular amplitude values or ranges of values indicative of a relative amount of ultrasonic energy, as a possible representation of any of the one-dimensional A-scan data samples.

Each geometric shape can then be rendered in the three-dimensional space with its corresponding size and color at 220. In order to exclude certain amplitude values that are unlikely to be indicative of a flaw in the test material, a predetermined gating value can be applied at 225. Setting a predetermined gating value in this manner will exclude rendering geometric shapes where the reflected energy is unlikely to be indicative of a flaw. The selection of the predetermined gating value will vary on several factors such as the type of test material that is being inspected, the type of flaws that one is looking for, and the experience of the ultrasonic inspection specialist using ultrasonic testing inspection system 100. For example, a gating value can be selected to a value that is known to be a threshold (e.g., 80%) at which geometric echoes (i.e., echoes caused by the geometry of the material being tested; reflections off the edges of the material, not caused by flaws or defects) may arise while performing a non-destructive testing operation of the test material. In one embodiment, only geometric shapes that correspond to amplitude values above this threshold will be displayed, while geometric shapes corresponding to values below the threshold will be excluded from the display. This will allow the ultrasonic inspection specialist to clearly identify flaws from geometrical echoes in real-time during the scanning of the test material.

A three-dimensional display of the data samples can then be generated at 230 after applying the predetermined gating value. Those skilled in the art will appreciate that the ultrasonic inspection specialist can increase or decrease the predetermined gating value depending on the circumstances in order to obtain a different perspective while analyzing the display to assess the presence of flaws in the test material.

In order to further assist the ultrasonic inspection specialist to clearly distinguish flaws and defects from geometrical echoes in real-time during the scanning of the test material, a three-dimensional model of the test material (a computer-aided-design model) can be integrated with the three-dimensional display of the data samples at 235. This provides an opportunity for the ultrasonic inspection specialist to validate whether any flaws that appear to be present in the three-dimensional visualization are indeed flaws. For example, if the three-dimensional model of the test material shows holes drilled in the material in the exact location that flaws are appearing in the three-dimensional visualization, then the ultrasonic inspection specialist would know that these drilled holes are designated to be in this location and are not necessarily indicative of flaws in the material.

The flow chart of FIG. 2 shows some of the processing functions associated with generating a three-dimensional visualization of one-dimensional A-scan data samples generated from an ultrasonic probe according to an embodiment of the present invention. In this regard, each block represents a process act associated with performing these functions. It should also be noted that in some alternative implementations, the acts noted in the blocks may occur out of the order noted in the figure or, for example, may in fact be executed substantially concurrently or in the reverse order, depending upon the act involved. Also, one of ordinary skill in the art will recognize that additional blocks that describe the processing functions may be added.

Figure 4:
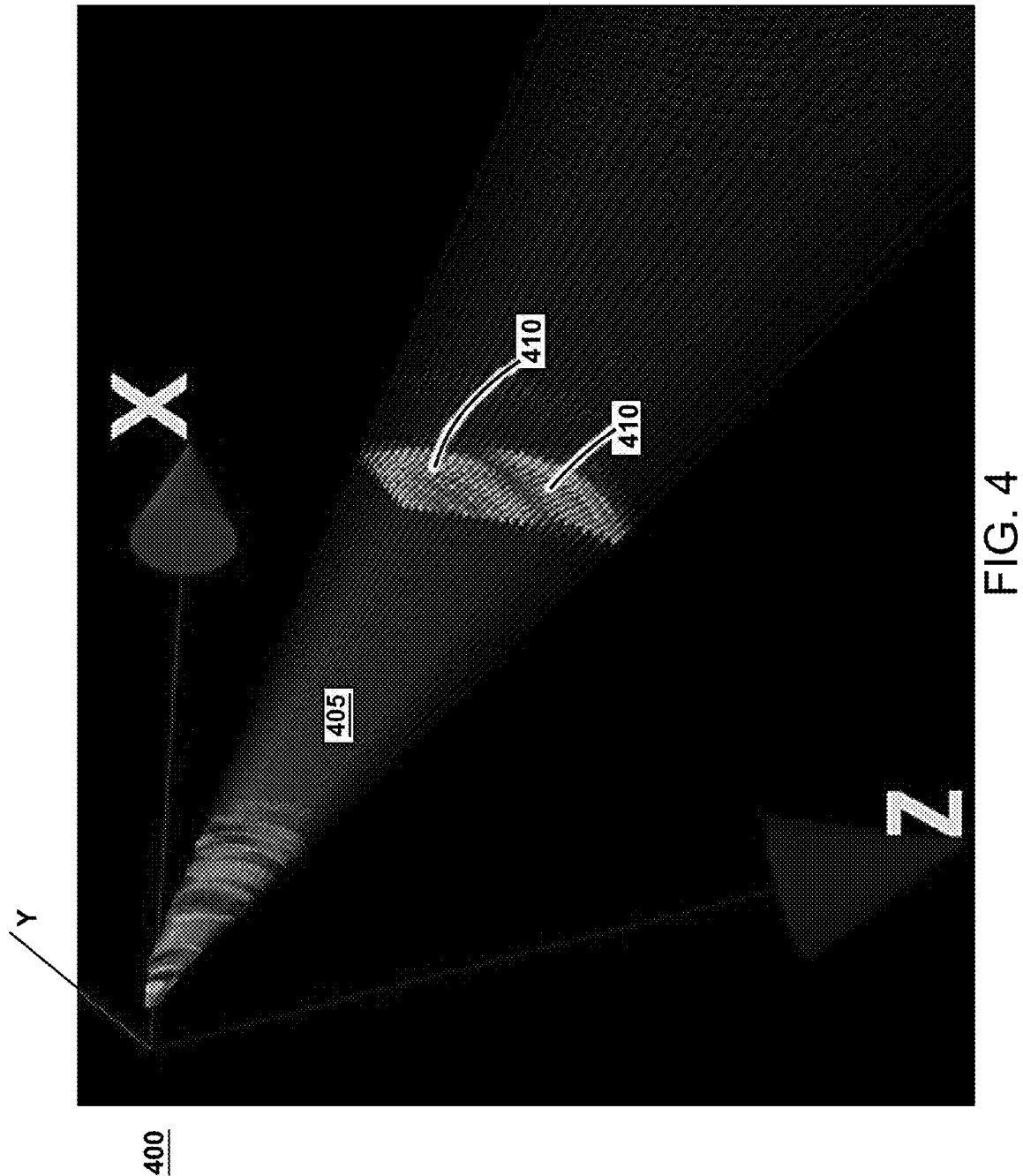
FIG. 4 shows an example of a three-dimensional A-scan display that can be generated according to an embodiment of the present invention.

FIG. 4 shows an example of a three-dimensional A-scan display 400 that can be generated according to an embodiment of the present invention. In this example, A-scan data values are displayed in their actual locations in a three-dimensional space defined by X, Y and Z vertices. Lines 405 represent the direction of the beam from the ultrasonic probe as it propagates through the test material. In this example, display 400 visualizes two holes 410 present in the test material. In one embodiment, signals that are reflected from the holes 410 are each displayed in this example with spherical shapes that are colored by a color map ranging from blue to yellow to red. This color is indicative of the amount of energy reflected back from the holes 410.

Figure 5:
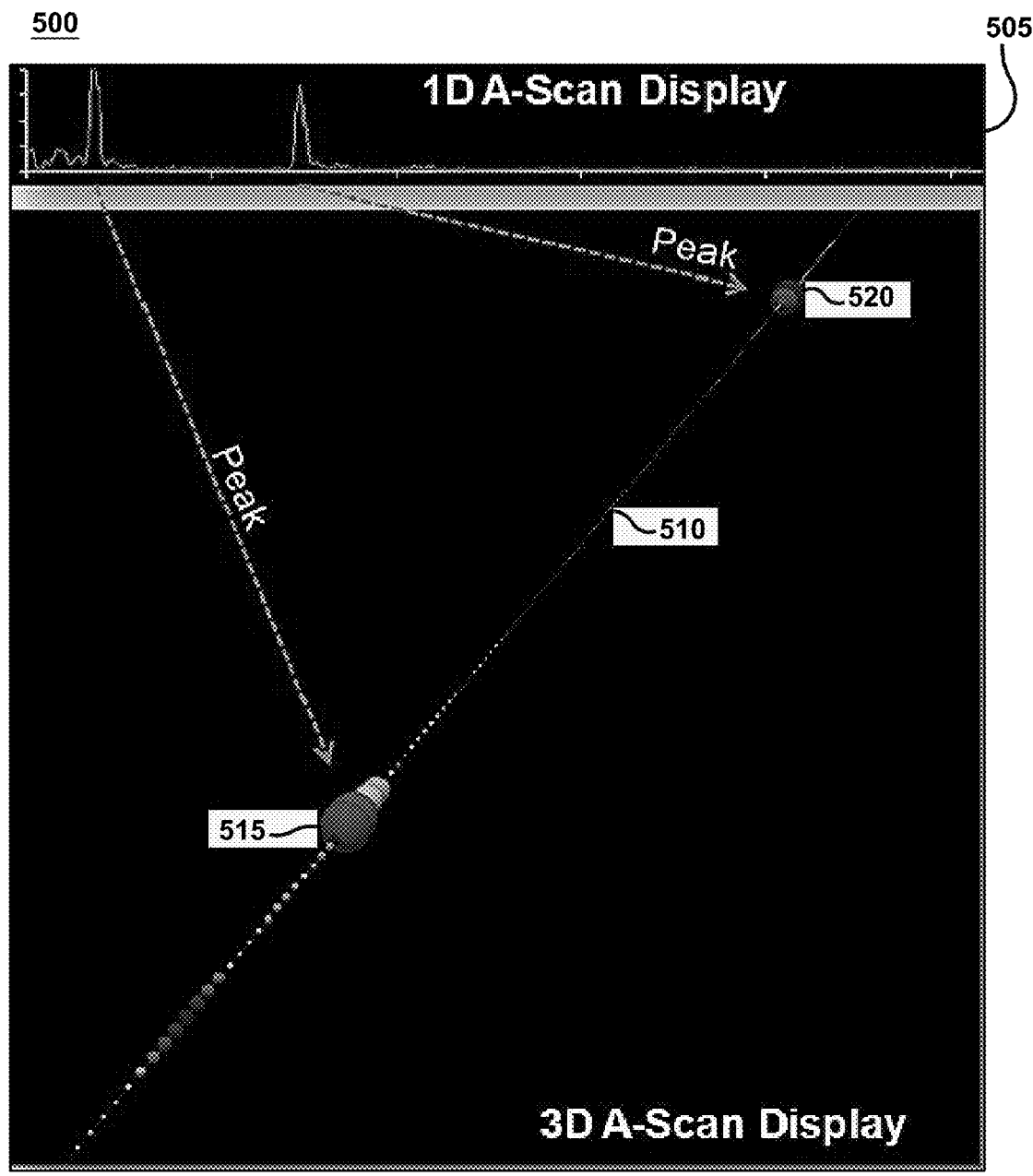
FIG. 5 shows an example of a traditional one-dimensional A-scan display transformed to a three-dimensional A-scan display according to an embodiment of the present invention.

FIG. 5 illustrates a relation between an original one-dimensional A-scan signal and the three-dimensional display that could be generated according to an embodiment of the present invention. In this example, display 500 contains a one-dimensional A-scan display 505 alongside a three-dimensional A-scan display 510 that has been transformed from the one-dimensional A-scan. As shown in FIG. 5, one-dimensional A-scan display 505 plots the amount of ultrasonic energy received from the test material versus a time of occurrence that the amount of ultrasonic energy is received back from the test material at the ultrasonic probe. All of the amplitude values shown in one-dimensional A-scan display 505 are transformed into three-dimensional A-scan display 510 as geometric objects each having a specified color that corresponds to the amplitude values in display 505. In this example, the geometric objects are rendered in three-dimensional A-scan display 510 as spheres. The peak amplitude values in one-dimensional A-scan display 505 are rendered in three-dimensional A-scan display 510 as spheres 515 and 520, which are larger in comparison to the other spheres corresponding to smaller amounts of reflected energy. Note that the location of each of the spheres in three-dimensional A-scan display 510 corresponds to the location within the test material in which these amplitude values were reflected. Also, after the predetermined gating value has been set, it is quite likely that the display will only show some of the larger spheres because the smaller spheres will not have a sufficient amount of energy to pass the threshold and warrant display as a possible flaw.

Figure 6A:
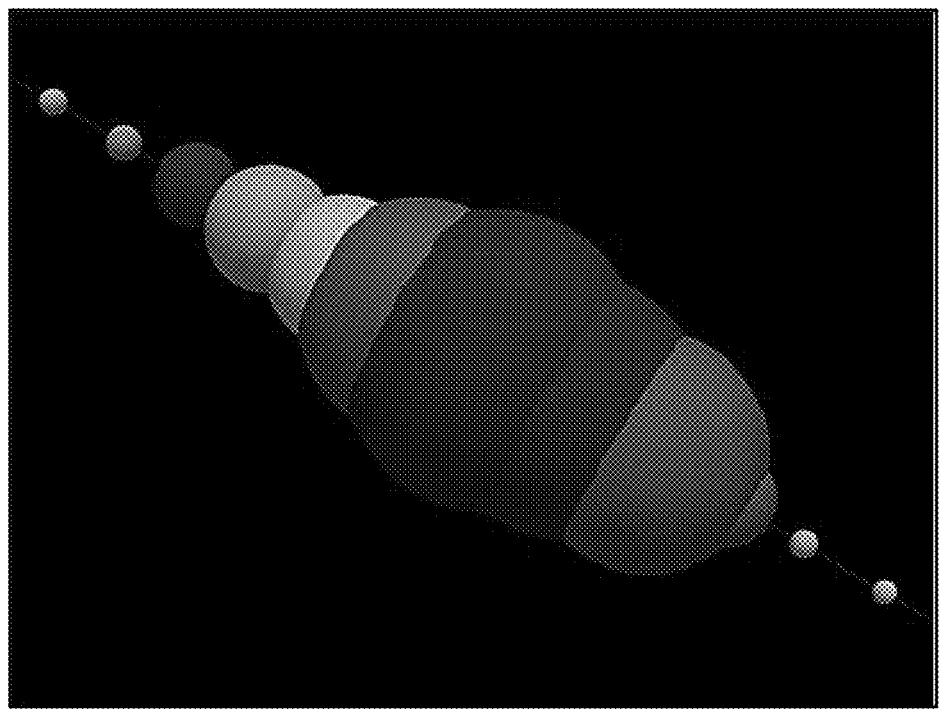
FIGS. 6A-6B show more detailed views of geometric shapes that can be used to represent a one-dimensional A-scan in a three-dimensional space according to embodiments of the present invention.
Figure 6B:
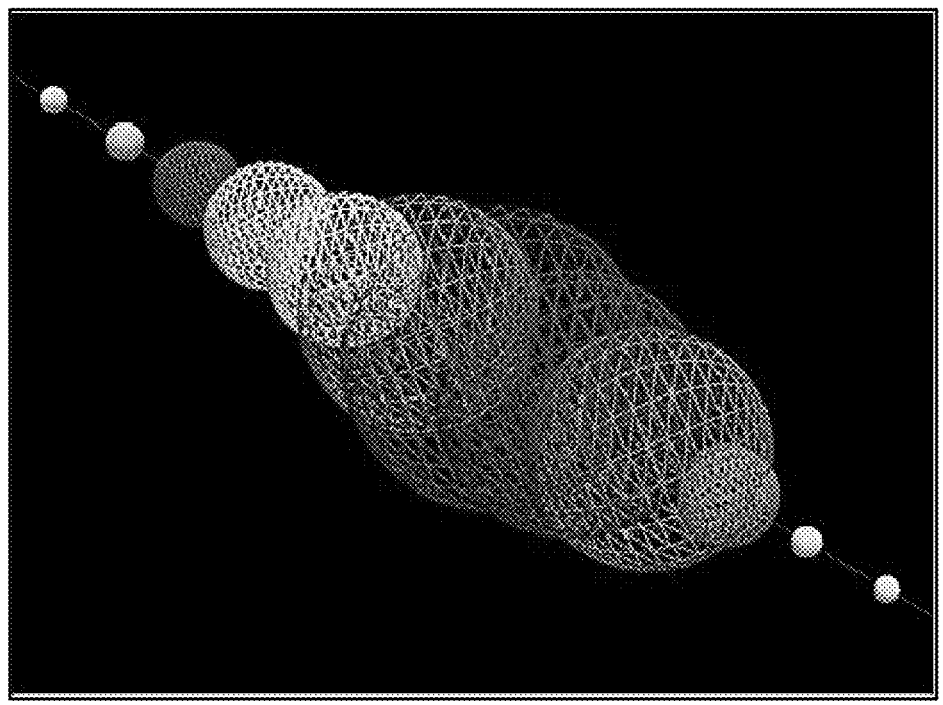

FIGS. 6A-6B show more detailed views of geometric shapes that can be used to represent a one-dimensional A-scan in a three-dimensional space according to an embodiment of the present invention. In particular, FIGS. 6A-6B show more detailed views of some of the larger spheres used in FIG. 5 to represent amplitude values captured in the one-dimensional A-scan data sample. FIGS. 6A-6B also show the spheres cross-hatched with different patterns to represent their different colors that translate to a corresponding amplitude value. As shown in FIGS. 6A-6B, the size of the spheres as defined by the radius or the diameter can be displayed to have solid color fills (FIG. 6A) or can be constructed as wire-frame spheres (FIG. 6B) each colored in the manner that corresponds to their respective amplitude value.

Figure 7B:
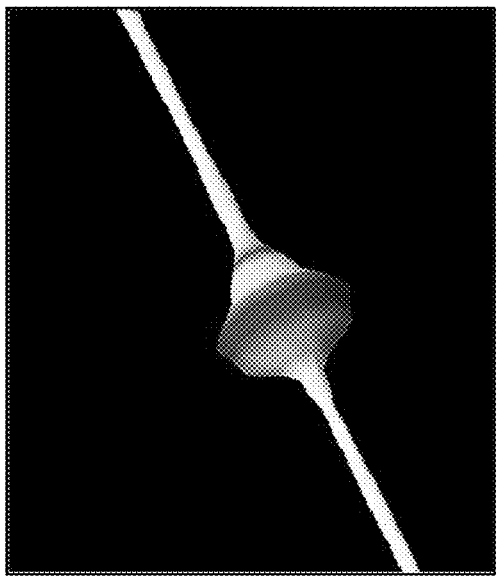
FIGS. 7A-7D show examples of alternative geometric shapes that can be used to represent a one-dimensional A-scan in a three-dimensional space according to embodiments of the present invention.
Figure 7D:
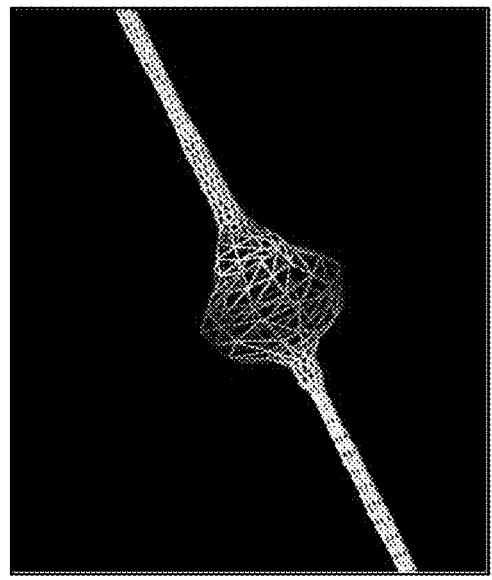
Figure 7A:
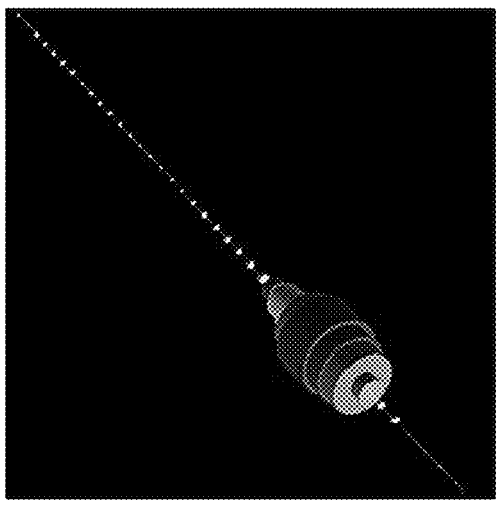
Figure 7C:
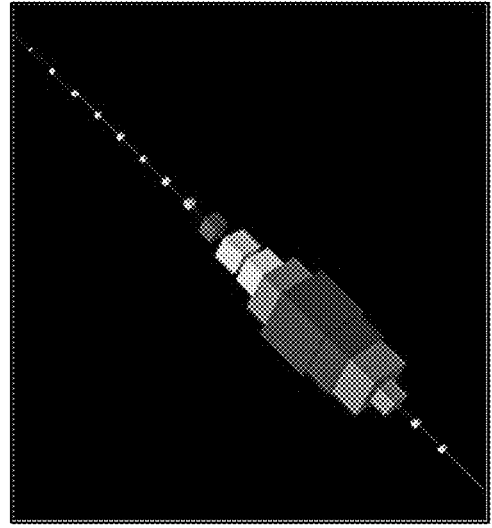

FIGS. 7A-7D show examples of alternative geometric shapes that can be used to represent a one-dimensional A-scan in a three-dimensional space. In FIG. 7A, the geometric shapes rendered in the three-dimensional space take the form of colored cylinders oriented in the direction of the beam of ultrasonic energy, wherein each of the different colored cylinders correspond to the amplitude values reflected in the A-scan data sample. In FIG. 7B, the geometric shapes in the display take the form of a tube with varying diameter and colored with different sections to represent the amplitude values reflected in the A-scan data sample. In FIG. 7C, the geometric shapes rendered in the three-dimensional space take the form of colored cubes oriented in the direction of the beam of ultrasonic energy, wherein each of the different colored cubes correspond to the amplitude values reflected in the A-scan data sample. In FIG. 7D, the geometric shapes in the display take the form of a wireframe version of the tube in FIG. 7B. These examples are not meant to be limiting, and those skilled in the art will appreciate that the amplitude values reflected in the one-dimensional A-scan data samples can be rendered in a three-dimensional space to have any one of a number of different shapes, sizes and colors.

Figure 8:
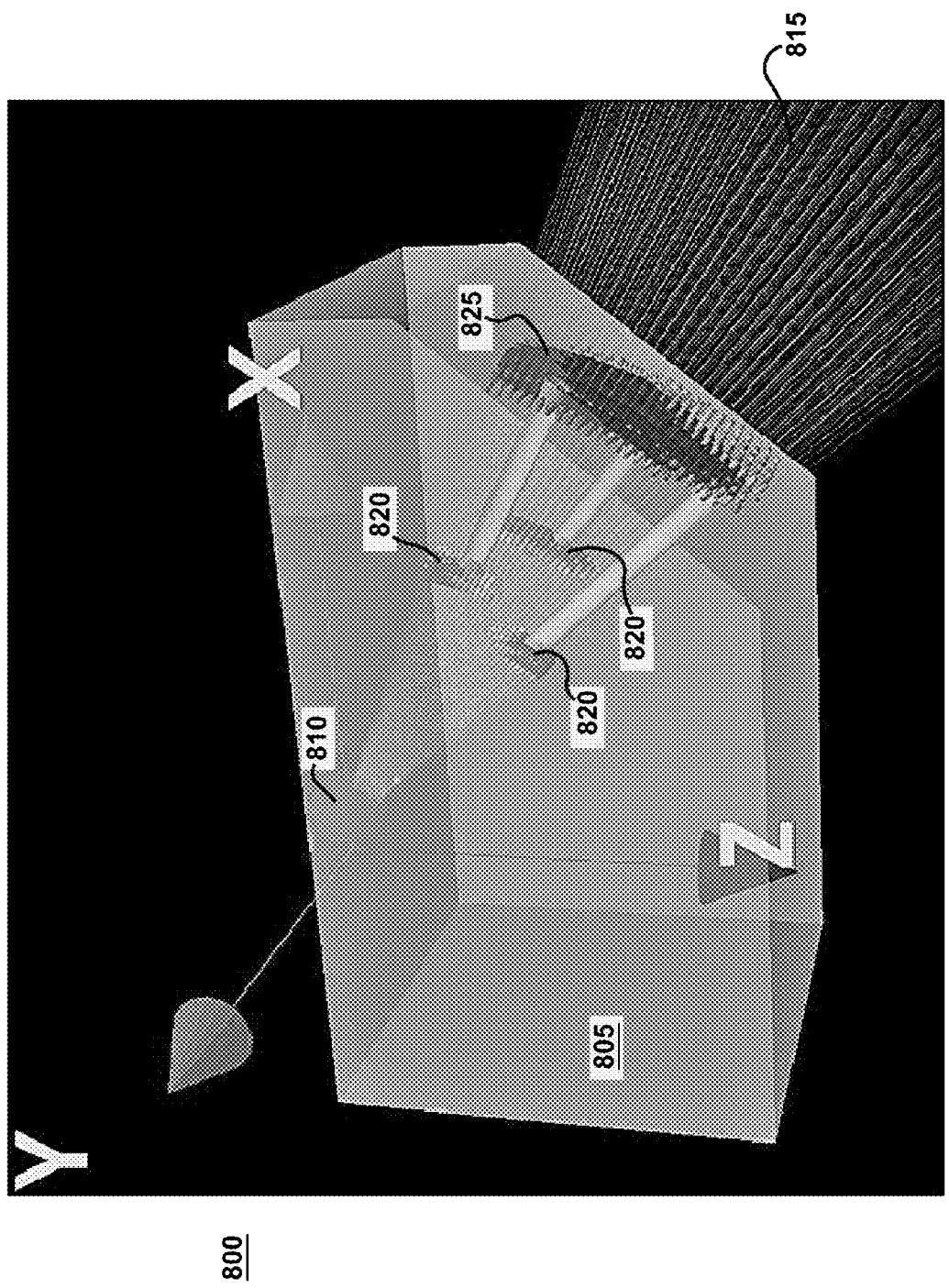
FIG. 8 shows an example of a three-dimensional A-scan display integrated with a three-dimensional model of a test material undergoing non-destructive testing with an ultrasonic probe according to an embodiment of the present invention.

FIG. 8 shows an example of a three-dimensional A-scan display 800 integrated with a three-dimensional model 805 of a test material undergoing non-destructive testing with an ultrasonic probe 810. In this example, A-scan data values are displayed in their actual locations in a three-dimensional space defined by X, Y and Z vertices. Lines 815 represent the direction of the beam from the ultrasonic probe 810 as it propagates through the test material. In this example, the three-dimensional A-scan display visualizes three holes 820 present in the test material. Because three-dimensional model 805 of a test material does not show the presence of holes, the holes can be indicative of a flaw in the material being inspected. Note that in three-dimensional A-scan display 800, area 825 which is cross-hatched to represent a certain amount of reflected energy would not be expected to indicate a flaw due to its position in relation to a side surface of the test material. Because area 825 abuts this side surface of the test material, this would likely be indicative of echoes from the back wall of the material and not a flaw in the material.

Figure 9:
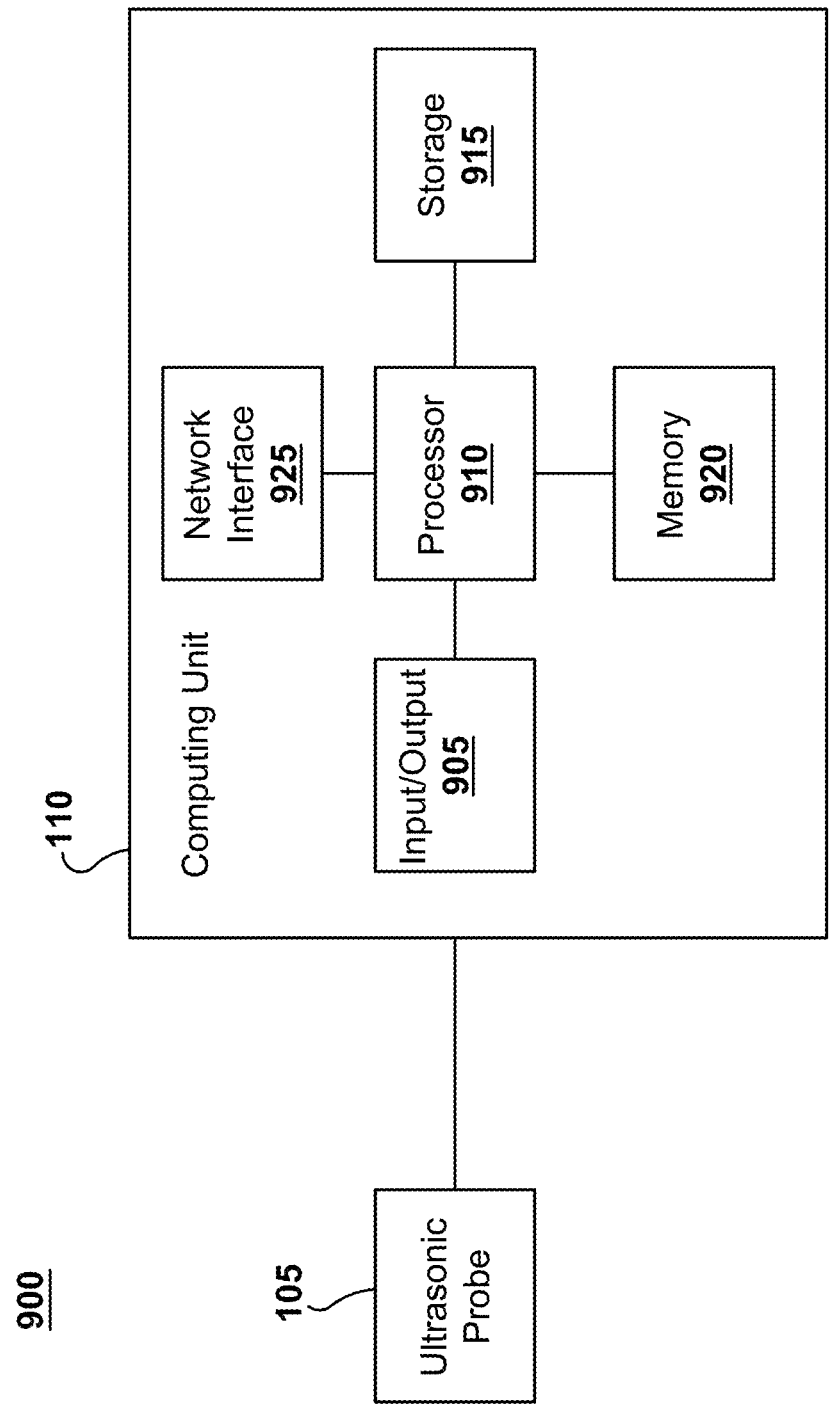
FIG. 9 shows a schematic block diagram illustrating the ultrasonic testing inspection system depicted in FIG. 1 that can provide three-dimensional visualization of A-scan data samples according to an embodiment of the present invention.

FIG. 9 shows a schematic block diagram 900 illustrating the ultrasonic testing inspection system depicted in FIG. 1 that can provide three-dimensional visualization of A-scan data samples according to the various embodiments of the present invention. In this high-level block diagram, ultrasonic probe 105 is in communication with computing unit 110 via an input/output component 905. Computing unit 110 contains a processor 910 which controls the overall operation of the computing unit by executing computer program instructions which define such operations. The computer program instructions may be stored in a storage device 915, or other computer readable medium, (e.g., magnetic disk) and loaded into memory 920 when execution of the computer program instructions is desired. Thus, method steps described above, including one or more of method steps illustrated in FIG. 2, may be defined by the computer program instructions stored in the memory 920 and/or storage device 915 and controlled by the processor 910 executing the computer program instructions. The computer program instructions may be implemented in software, which includes but is not limited to firmware, resident software, microcode, etc. Furthermore, the computer program instructions can take the form of a computer program product accessible from a computer-usable or computer-readable medium providing program code for use by or in connection with a computer or any instruction execution system (e.g., processing units).

The computing unit 110 also can include one or more network interfaces 925 for communicating with other devices via a network. Input/output devices 905 can also be used to enable user interaction with the computing unit 110 (e.g., display, keyboard, mouse, speakers, buttons, etc.). For example, input/output device 905 could be used to provide three-dimensional visualization of the A-scan data sample acquired by ultrasonic probe 105. One skilled in the art will recognize that an actual implementation of computing unit 110 could contain other components as well, and that FIG. 9 is a high level representation of only some of the components of such a computing unit for illustrative purposes.

As described herein, technical effects of the various embodiments of the present invention include, but are not limited to, providing a technique for real-time three-dimensional visualization of one-dimensional A-scan data samples generated from a multiple of ultrasonic probes that can include two-dimensional probe arrays, one-dimensional phased-array probes, and single element probes. The real-time three-dimensional visualization of one-dimensional A-scan data samples is well suited for use with portable ultrasonic testing inspection systems that have the hardware that is sufficient for performing the visualization techniques described herein, including graphics processors to display the one-dimensional A-scan data samples in a three-dimensional space. Furthermore, the three-dimensional visualization techniques described herein are well suited for non-destructive testing of various materials (e.g., locating flaws) since the displays can show the actual position of flaws in the materials including the maximum amplitudes of ultrasonic energy associated with these flaws without losing depth information.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises," "comprising," "includes," "including," and "having," when used in this specification, specify the presence of stated features, integers, steps, operations, elements, and/or components, but do not preclude the presence or addition of one or more other features, integers, steps, operations, elements, components, and/or groups thereof. It is further understood that the terms "front" and "back" are not intended to be limiting and are intended to be interchangeable where appropriate While the disclosure has been particularly shown and described in conjunction with a preferred embodiment thereof, it will be appreciated that variations and modifications will occur to those skilled in the art. Therefore, it is to be understood that the appended claims are intended to cover all such modifications and changes as fall within the spirit of the disclosure and the language of the claims.

What is claimed is:

1. A computer-implemented method, comprising: using a computing unit to perform actions comprising:

obtaining a plurality of one-dimensional A-scan data samples from an ultrasonic probe, each data sample representing ultrasonic signals received from a test material undergoing non-destructive testing, wherein each data sample indicates an amount of ultrasonic energy received from the test material at a time of occurrence;

transforming the plurality of data samples into a three-dimensional space to generate a three-dimensional visualization of the ultrasonic signals without performing a volume reconstruction, wherein each of the plurality of data samples are rendered as a geometric shape representing an amplitude of the ultrasonic signal in the three-dimensional space; and displaying the plurality of geometric shapes.

2. The method according to claim 1, wherein the transforming comprises:
- determining a position of each data sample in the three-dimensional space, the position of each data sample representative of a location of a point of reflection within the test material; and
- generating a geometric shape for each determined position, the geometric shape characterized by a certain size and color corresponding to an amplitude value indicative of the amount of received ultrasonic energy as represented in the data sample for the determined position.

3. The method according to claim 2, wherein the determining of a position of each data sample is computed as a function of a beam entry point indicating a location that beams of ultrasonic energy entered the test material, one or more beam angles that indicate direction of travel of the beams of the ultrasonic energy in the test material, and a velocity of sound of the beams of the ultrasonic energy in the test material.

4. The method according to claim 2, wherein larger-sized geometric shapes are indicative of larger amplitude values as compared to smaller-sized geometric shapes that are indicative of smaller amplitude values.

5. The method according to claim 2, wherein the generating of a geometric shape comprises applying a color map containing a plurality of colors each corresponding to a particular amplitude value range indicative of an amount of ultrasonic energy.

6. The method according to claim 2, further comprising setting a predetermined gating value that excludes geometric shapes from being rendered in the three-dimensional space that correspond to an amplitude value that is deemed unlikely to be indicative of a flaw in the test material.

7. The method according to claim 6, wherein the displaying of the plurality of data samples as transformed into the three-dimensional space with the geometric shapes rendered therein comprises applying the predetermined gating value to distinguish any flaws present in the test material from geometric echoes.

8. The method according to claim 1, wherein the displaying of the plurality of data samples as transformed into the three-dimensional space with the geometric shapes rendered therein further comprises integrating a three-dimensional model in the three-dimensional space.

9. The method according to claim 1, wherein the transforming of each of the plurality of data samples into a three-dimensional space occurs without reconstructing a physical beam geometry.

10. An ultrasonic testing inspection system, comprising:
- an ultrasonic probe array configured to scan a test material with a beam of ultrasound energy that propagates therethrough and receive ultrasonic signals reflected back from the test material, the ultrasonic signals containing a volume of data representative of the test material;
- a computing unit configured to receive the ultrasonic signals from the ultrasonic probe in a form of a plurality of one-dimensional A-scan data samples, wherein each data sample indicates an amount of ultrasonic energy received from the test material at a time of occurrence, and the computing unit further configured to transform the data samples into a three-dimensional space to generate a three-dimensional visualization of the ultrasonic signals without performing a volume reconstruction, wherein each of the data samples are rendered as a geometric shape representing an amplitude of the ultrasonic signal in the three-dimensional space; and
- a display configured to generate a display in real-time of the plurality of geometric shapes.

11. The ultrasonic testing inspection system according to claim 10, wherein the transformation of the data samples into a three-dimensional space by the computing unit comprises:
- determining a position of each data sample in the three-dimensional space, the position of each data sample representative of a location of a point of reflection within the test material; and
- generating a geometric shape for each determined position, the geometric shape characterized by a certain size and color corresponding to an amplitude value indicative of the amount of received ultrasonic energy as represented in the data sample for the determined position.

12. The ultrasonic testing inspection system according to claim 11, wherein the determining of a position of each data sample is computed as a function of a beam entry point indicating a location that beams of ultrasonic energy entered the test material, one or more beam angles that indicate direction of travel of the beams of the ultrasonic energy in the test material, and a velocity of sound of the beams of the ultrasonic energy in the test material.

13. The ultrasonic testing inspection system according to claim 11, wherein larger-sized geometric shapes are indicative of larger amplitude values as compared to smaller-sized geometric shapes that are indicative of smaller amplitude values.

14. The ultrasonic testing inspection system according to claim 11, wherein the generating of a geometric shape comprises applying a color map stored in memory of the computing unit that contains a plurality of colors each corresponding to particular amplitude value range indicative of an amount of ultrasonic energy.

15. The ultrasonic testing inspection system according to claim 11, wherein the computing unit is further configured to set a predetermined gating value that excludes geometric shapes from being rendered in the three-dimensional space correspond to an amplitude value that is deemed unlikely to be indicative of a flaw in the test material.

16. The ultrasonic testing inspection system according to claim 15, wherein the display is configured to apply the predetermined gating value to distinguish any flaws present in the test material from geometric echoes.

17. The ultrasonic testing inspection system according to claim 10, wherein the computing unit is further configured to store a three-dimensional model representative of the test material.

18. The ultrasonic testing inspection system according to claim 17, wherein the display unit is configured to integrate the three-dimensional model of the test material in the three-dimensional space.

19. A non-transitory computer readable medium storing computer instructions, which when executed, enables an ultrasonic testing inspection system to perform a method for visualizing a plurality of one-dimensional A-scan data samples in a three-dimensional space, the method comprising:
- obtaining a plurality of one-dimensional A-scan data samples from an ultrasonic probe, each data sample representing ultrasonic signals received from a test material undergoing non-destructive testing, wherein each data sample indicates an amount of ultrasonic energy received from the test material at a time of occurrence;
- transforming the plurality of data samples into a three-dimensional space to generate a three-dimensional visualization of the ultrasonic signals without performing a volume reconstruction, wherein each of the plurality of data samples are rendered as a geometric shape representing an amplitude of the ultrasonic signal in the three-dimensional space without reconstructing a physical beam geometry; and generating a display that visualizes the geometric shapes.

20. The non-transitory computer readable medium according to claim 19, wherein the transforming comprises:

determining a position of each data sample in the three-dimensional space, the position of each data sample representative of a location of a point of reflection within the test material; and generating a geometric shape for each determined position, the geometric shape characterized by a certain size and color corresponding to an amplitude value indicative of the amount of received ultrasonic energy as represented in the data sample for the determined position.

21. The non-transitory computer readable medium according to claim 20, wherein the determining of a position of each data sample is computed as a function of a beam entry point indicating a location that beams of ultrasonic energy entered the test material, one or more beam angles that indicate direction of travel of the beams of the ultrasonic energy in the test material, and a velocity of sound of the beams of the ultrasonic energy in the test material.

22. The non-transitory computer readable medium according to claim 20, wherein larger-sized geometric shapes are indicative of larger amplitude values as compared to smaller-sized geometric shapes that are indicative of smaller amplitude values.

23. The non-transitory computer readable medium according to claim 20, wherein the generating of a geometric shape comprises applying a color map containing a plurality of colors each corresponding to a particular amplitude value range indicative of an amount of ultrasonic energy.

24. The non-transitory computer readable medium according to claim 20, further comprising setting a predetermined gating value that excludes geometric shapes from being rendered in the three-dimensional space that correspond to an amplitude value that is deemed unlikely to be indicative of a flaw in the test material.

25. The non-transitory computer readable medium according to claim 24, wherein the displaying of the data samples as transformed into the three-dimensional space with the geometric shapes rendered therein comprises applying the predetermined gating value to distinguish any flaws present in the test material from geometric echoes.

26. The non-transitory computer readable medium according to claim 19, wherein the displaying of the plurality of data samples as transformed into the three-dimensional space with the geometric shapes rendered therein further comprises integrating a three-dimensional model in the three-dimensional space.

* * * * *